United States Patent [19]
Roberts

[11] Patent Number: 6,087,396
[45] Date of Patent: Jul. 11, 2000

[54] OXYBUTYNIN FORMULATIONS AND METHOD OF USE

[75] Inventor: Dennis H. Roberts, Decatur, Ill.

[73] Assignee: Situs Corporation, Solana Beach, Calif.

[21] Appl. No.: 09/231,139

[22] Filed: Jan. 15, 1999

Related U.S. Application Data

[60] Provisional application No. 60/103,228, Oct. 5, 1998.

[51] Int. Cl.$^7$ .................................................... A01N 37/12
[52] U.S. Cl. ........................ 514/534; 514/544; 514/549; 424/422; 424/423; 424/430; 600/29; 600/30; 600/31; 604/264; 604/275; 604/285; 604/288; 604/892.1
[58] Field of Search .................................... 514/534, 544, 514/549; 600/29, 30, 31; 604/264, 275, 285, 288, 892.1; 424/422, 423, 430

[56] References Cited

U.S. PATENT DOCUMENTS

| | | | |
|---|---|---|---|
| 4,327,725 | 5/1982 | Cortese et al. | 424/427 |
| 4,519,801 | 5/1985 | Edgren | 424/425 |
| 4,612,008 | 9/1986 | Wong et al. | 604/892.1 |
| 4,783,337 | 11/1988 | Wong et al. | 424/468 |
| 5,082,668 | 1/1992 | Wong et al. | 424/473 |
| 5,399,359 | 3/1995 | Baichwal | 424/464 |
| 5,674,895 | 10/1997 | Guittard et al. | 514/534 |

OTHER PUBLICATIONS

Brendler, et al., Topical Oxybutynin Chloride for Relaxation of Dysfunctional Bladders, *J. of Urology* 141:1350–1352; 1989.

Bonney, et al., Topical Effect of Intravesical Oxybutynin, *J. of Urology* 150:1522–1525; 1993.

Conner, et al., Early Cystometrograms Can Predict the Response to Intravesical Instillation of Oxybutynin Chloride in Myelomeningocele Patients, *J. of Urology* 151:1045–1047; 1994.

Greenfield, et al., The Use of Intravesical Oxybutynin chloride in Children with Neurogenic Bladder, *J. of Urology* 146:532–534; (1991).

Kaplinsky, et al., Expanded Followup of Intravesical Oxybutynin Chloride Use in Children with Neurogenic Bladder, *J. of Urology* 156:753–756; (1996).

Madersbacher, M.D., et al., Control of Detrusor Hyperreflexia by the Intravesical Instillation of Oxybutynine Hydrochloride, *Paraplegia* 29:84–90; (1991).

Massad, et al., The Pharmacokinetics of Intravesical and Oral Oxybuytnin Chloride, *J. of Urology* 148:595–597 (1992).

Painter, et al., Long–Term Intravesical Oxybutynin Chloride Therapy in Children with Myelodysplasis, *J. of Urology* 156:1459–1462 (1996).

Palmer, et al., Complications of Intravesical Oxybutynin Chloride Therapy in the Pediatric Myelomeningocele Population, *J. of Urology* 157:638–640 (1997).

Prasad, et al., Intravesical Oxybutynin Chloride and Clean Intermittent Catheterisation in Patients with Neurogenic Vesical Dysfunction and Decreased Bladder Capacity, *British J. of Urology* 72:719–722 (1993).

Weese, M.D., et al., Intravesical Oxybutynin Chloride: Experience with 42 Patients, *Urology* 41(6):527–530; (1993).

*United States Official Monographs* 23:1127–1129; (1992).

Barion et al., Oxybutyninlosung zur Instillation in die Blase, *Krankenhaus Pharmazie* 18/4:171–172 (1997) English Abstract.

Buyse, et al., Intraesical Application of a Stable Oxybutynin Solution Improves Therapeutic Compliance and Acceptance in Children with Neurogenic Bladder Dysfunction, *J. of Urology* 160:1084–1087 (1998).

Yokoyama, et al., Urodynamic Effects of Intravesical Oxybutynin Chloride in Conscious Rats, *J. of Urology* 155:768–771 (1996).

Nunn, et al., Buffer Helps Stabilise Oxybutynin, database Embase "Online!" Abstract, (1994).

*Primary Examiner*—Frederick Krass
*Attorney, Agent, or Firm*—Knobbe, Martens, Olson & Bear, LLP

[57] ABSTRACT

Oxybutynin chloride formulations having increased stability at body temperature, even at high concentrations. These formulations comprise oxybutynin chloride at a pH of between 3.0 and 5.0, and may include a buffer capable of providing adequate buffering capacity in this range. The OC solutions can be placed in an infuser device for treatment of bladder dysfunction.

16 Claims, No Drawings

OXYBUTYNIN FORMULATIONS AND METHOD OF USE

RELATED APPLICATIONS

This application claims priority under 35 USC §119(e) to U.S. Provisional Application Ser. No. 60/103,228, filed Oct. 5, 1998.

FIELD OF THE INVENTION

The present invention relates to oxybutynin formulations which are stable at body temperature and their use in treating bladder dysfunction. These formulations are suitable for extended diffusion into the bladder using infuser devices.

BACKGROUND OF THE INVENTION

Patients with various bladder disorders including hyperreflexic voiding dysfunction and secondary urge incontinence are typically treated with anticholinergic and antispasmodic agents, such as oxybutynin chloride (benzeneacetic acid, α-cyclohexyl-α-hydroxy-, 4-(diethylamino)-2-butynyl ester hydrochoride, (±)). Oxybutynin chloride (OC) is available in syrup and table form (United States Pharmacopoeia Official Monographs 23:1127–1129). However, many patients do not respond to these medications when taken orally or have unacceptable side effects that limit their use. Such side effects include dryness of the mouth, disturbance of accommodation and increased constipation.

OC has been administered directly to the bladder via a catheter (intravesical administration). Brendler et al. (J. Urology 141:1350–1352, 1989) dissolved 5 mg. tablets of OC in water and instilled the resulting solution via a catheter into the bladder of patients with persistent urge incontinence twice daily. The solution was retained for 30 minutes. Madersbacher et al. (Paraplegia 29:84–90, 1991) instilled the same OC solution via catheter into the bladder to treat detrusor hyperreflexia in patients with spinal cord lesions. Greenfield et al. (J. Urology 146:532–534, 1991) dissolved 5 mg. tablets of OC in 10 ml of saline and administered the resulting solution via catheter to the bladder of patients with hypertonic, hyperreflexive bladders. Massad et al. (J. Urology 143:595–597, 1992) examined the pharmacokinetics of intravesical and oral OC. Oxybutinin chloride tablets were crushed and dissolved in sterile water (7.5 mg/30 ml). The resulting solution was administered orally or intravesically to patients with uninhibited detrusor activity and/or poor bladder compliance. The authors concluded that intravesical OC was well tolerated, efficacious and rapidly absorbed, resulting in plasma concentrations markedly higher than after oral administration. Weese et al. (Urology 41:527–530, 1993) dissolved 5 mg OC tablets in 30 cc sterile water and instilled the resulting solution into the bladders of patients who were incontinent secondary to uninhibited detrusor contractions and had failed oral anticholinergic therapy. Other studies have also been described using OC tablets dissolved in water or saline for installation into the bladder of patients with bladder dysfunction (Prasad et al., British J Urology 72:719–722, 1993; Connor et al., J. Urology 151:1045–1047, 1994; Kaplinsky et al., J. Urology 156:753–756, 1996; Painter et al., J Urology 156:1459–1462, 1996; Palmer et al., J Urology 157:638–640, 1997). In all of these studies, OC tablets are dissolved in saline or water at a near neutral pH, delivered to the bladder via a catheter, and allowed to remain in the bladder for several hours prior to removal. In these studies, the concentration range of OC used was between 0.17 and 0.5 mg/ml. Bonney et al., J. Urology 150:1522–1525, 1993, intravesically administered OC dissolved in sterile saline to rats at three doses: 0.25 mg/ml, 2.5 mg/ml and 25 mg/ml, to determine the effects of drug concentration on mucosal or bladder wall change, and on urinary infection. The authors concluded that in the highest dose group (25 mg/ml), systemic absorption from the bladder caused weight loss and cachexia.

Although the OC solutions described above are suitable for temporary installation into the bladder, they are not sufficiently stable for extended delivery into the bladder over several weeks or months. The present invention provides stable OC compositions for use in intravesical infuser devices for extended diffusion into the bladder.

SUMMARY OF THE INVENTION

One embodiment of the present invention is a pharmaceutical composition comprising oxybutynin chloride, wherein the composition is stable at 37° C. for at least 12 hours when placed within the bladder. Preferably, the oxybutynin chloride has a concentration of between about 1 mg/ml and 30 mg/ml. More preferably, the concentration of oxybutynin chloride is between about 10 mg/ml and 25 mg/ml. Most preferably, the concentration of oxybutynin chloride is about 20 mg/ml. In another aspect of this preferred embodiment, the composition has a pH of between about 3.0 and 5.0; preferably between about 3.5 and 4.5; more preferably about 4.0. The composition may further comprise a buffering agent having a concentration of between about 0.005 M and 0.1 M. Preferably, the buffering agent has a concentration of between about 0.01 and 0.05 M. In one aspect of this preferred embodiment, the buffering agent is acetate or citrate. The composition may further comprise a cosolvent. Preferably, the cosolvent is a viscosity-enhancing agent. In another aspect of this preferred embodiment, the viscosity-enhancing agent is a carbohydrate or cellulosic viscosity enhancing agent, such as carboxymethylcellulose or hydroxypropylmethylcellulose. The composition may be provided in combination with an infuser capable of releasing the composition at a particular flow rate. Preferably, the infuser is an intravesical infuser. Advantageously, the flow rate is less than about 400 μl/hour.

The present invention also provides a method for treating a bladder disorder, comprising the steps of: placing the intravesical infuser in the bladder; and placing the pharmaceutical composition described above in the intravesical infuser. Preferably, the bladder disorder is secondary urge incontinence, hyperreflexive voiding dysfunction, neurologic bladder or decreased bladder capacity.

DETAILED DESCRIPTION OF THE PREFERRED EMBODIMENTS

The present invention provides stable, autoclavable OC pharmaceutical compositions for use in an infuser. The infuser pump may be placed outside the body and attached to a catheter for instillation of the composition into the bladder. In a preferred embodiment, the composition is placed in an intravesical infuser. These compositions are stable to increased temperature (up to at least 50° C. for at least 3 weeks), autoclaving, and to contact with parts of an intravesical infuser. One preferred intravesical infuser is described in copending U.S. patent application Ser. No. 09/041,475, filed Mar. 11, 1998, the entire contents of which are hereby incorporated by reference. The excellent temperature and contact stability of the present OC compositions allows extended delivery into the bladder for days, weeks or months, compared to previous OC compositions which do not exhibit such stability and are typically retained within the bladder for several hours. The increased stability is due to several factors, including concentration of OC, pH and buffer concentration. Thus, the OC compositions of the invention are well suited for use in the bladder due to their increased stability at both ambient and body temperature (Example 1).

In another preferred embodiment, the OC compositions of the invention are stable at body temperature for at least 12, 24 or 48 hours. In a more preferred embodiment, the compositions are stable at body temperature for at least 3–7 days. In a most preferred embodiment, the compositions are stable at body temperature for about 7, 14, 21 or 28 days. The term "stable" as used herein indicates that preferably no more than 5%, more preferably no more than 3%, and most preferably no more than 1% of the OC in the composition is degraded while present in the bladder.

In a preferred embodiment, the OC composition is an aqueous solution. In another preferred embodiment, the concentration of OC in solution, is between about 0.1 mg/ml, 0.3 mg/ml, 0.5 mg/ml, 0.8 mg/ml, 1 mg/ml, 5 mg/ml or 10 mg/ml, and 30 mg/ml. In a more preferred embodiment, the concentration is between about 10 mg/ml and about 25 mg/ml. In a most preferred embodiment, the concentration is about 20 mg/ml. If the concentration is too low, one cannot deliver the desired dosage of OC over an extended time with a reasonably-sized device. If the concentration of OC is too high, it will be insoluble and will precipitate out of solution.

There is a sharp drop in the solubility of OC at a pH higher than 5.0. In the absence of a cosolvent, the solubility at pH 6.0 is 2 mg/ml, and the solubility at pH 7.0 is less than 1 mg/ml. Accordingly, in a preferred embodiment, the pH of the OC 25 composition is between about 3.0 and about 5.0; preferably between about 3.5 and 4.5; more preferably, about 4.0.

In another preferred embodiment, OC is provided in a buffer capable of providing adequate buffering capacity at a pH between about 3.0 and 5.0. Suitable buffers include citrate and acetate. The buffer concentration is typically between about 0.005 M and 0.1 M, preferably between 0.01 M and 0.05 M, more preferably about 0.01 M.

The OC compositions of the invention may further include a cosolvent. Suitable cosolvents include glycol cosolvents such as glycerol and propylene glycol, which also serve as viscosity-enhancing (thickening) agents. In a preferred embodiment, the cosolvent is a carbohydrate or cellulosic viscosity-enhancing agent such as carboxymethylcellulose, hydroxypropylmethylcellulose, or any other viscosity-enhancing agent well known in the art, to help control the flow rate of the OC from the infuser. In another preferred embodiment, the viscosity-enhancing agent is a non-sugar. Complex carbohydrates are considered to be non-sugars, whereas mono- and di-sacharides are considered to be sugars. In a preferred embodiment, the viscosity of the composition is between about 10 cps and 100 cps (centipoise), corresponding to between about 0.5% and 2.0% thickening agent. More preferably, the viscosity is between about 25 cps and 75 cps. Most preferably, the viscosity is between about 40 cps and 60 cps. In another preferred embodiment, the flow rate of the composition from the infuser is within the range of 0.1, 1, 5, 10, 25, 50, 75, 100, 150 or 200, 300 or 400 µl/hour.

The OC-containing pharmaceutical compositions of the invention are formulated with pharmaceutically acceptable carriers such as water, Ringer's solution and isotonic sodium chloride solution using methods well known in the art. The compositions may further include one or more of a demulcent, stabilizer, preservative, coloring agent, or any other additive conventional in the art. For assistance in formulating the compositions of the present invention, one may refer to Remington's Pharmaceutical Sciences, 15th Edition, Mack Publishing Co., Easton, Pa.

Syrups are pharmaceutical formulations or solutions for oral administration which are sweet and viscid, typically containing one or more sugars in sweetening agents such as sucrose, sorbitol or glycerol in an amount from about 1% to near saturation. In a preferred embodiment, the OC composition of the invention is not a syrup and contains essentially no sweetening agents. If present, the concentration of these sugars or sweetening agents is significantly less than the concentration of OC or of buffer salts (e.g., 0.01%–0.1%).

The OC compositions of the invention are used to treat bladder dysfunction including secondary urge incontinence, hyperreflexive voiding dysfunction, neurogenic bladder and decreased bladder capacity. In a preferred embodiment, an intravesical infuser is inserted into the bladder via the urethra, and the OC compositions are placed in the intravesical infuser. The OC continuously diffuses out of the infuser over the course of several weeks or months to provide a maximum therapeutic benefit. This is possible because of the high concentration and the stability of the OC compositions of the invention.

Formulation studies were conducted to develop a stable formulation of oxybutynin chloride solution for use in dosing and toxicity studies. The initial stability study was performed on various formulations of OC solutions (Reference No. RD186072). Initial formulations containing 20 mg/ml OC were compounded at pH 3.0, 4.0 and 5.0. A formulation containing citrate buffer was also tested. These formulations are shown in Table 1.

TABLE 1

| Ingredient | RD186072-1 | RD186072-2 | RD186072-3 | RD186072-5 |
|---|---|---|---|---|
| Oxybutynin Chloride | 2 g | 2 g | 2 g | 2 g |
| Sodium Chloride | 0.6 g | 0.6 g | 0.6 g | 0.06 g |
| Citric acid | — | — | — | 1.2 g |
| Sodium Citrate | — | — | — | 1.2 g |
| Qs pH with 1N HCl/1N NaOH to | 3.0 | 4.0 | 5.0 | 4.0 |
| Water for Injection | qs to 100 mL | qs to 100 mL | qs to 100 mL | qs to 100 mL |

EXAMPLE 1

Stability of OC Solutions

Three OC solution formulations (RD186072-1, RD186072-2 and RD186072-3) were compounded and placed in 10 ml clear glass vials sealed with a Teflon faced stopper. The filled units were incubated at 40° C. and 50° C., then assayed for OC at one week and three weeks using high performance liquid chromatography (HPLC) using a 150× 4.6 mm, octadecyl (C18) stationary phase, base-deactivated silica, 5 µm particle size (BDS Hypersil C18 or equivalent). HPLC was performed as follows. A pH=7.0 buffer was prepared by dissolving 6.8 g of potassium phosphate monobasic in 1 liter of water, followed by addition of 5 ml triethylamine and adjustment of the pH to 7.0±0.1 with phosphoric acid. The mobile phase consisted of 600 ml aceotonitrile and 400 ml of buffer, pH 7.0. The HPLC system was prepared with the following parameters: wavelength, 220 nm; injection volume, 10 μl; column temperature, 40° C.; flow rate, 2 ml/min. The working standard solution was prepared by accurately weighing approximately 30 mg oxybutynin reference standard, transferring to a 25 ml volumetric flask and diluting to volume with acetonitrile. The concentration of OC was calculated as follows: [OC]=(weight, mg)(assay factor)/(25.0 ml). OC solution (3.0 ml) was transferred into a 50 ml volumetric flask and diluted to volume with acetonitrile (dilution factor=16.67). The working standard was injected and the mobile phase adjusted if necessary to meet the following suitability requirements for the oxybutynin peak: theoretical plates, $\geq 3,000$; tailing factor, $\leq 2.0$. Five replicate injections of the working standard were performed and the oxybutynin peak responses as area were recorded. The relative standard deviation (RSD) of the replicate areas was $\leq 2.0\%$. Duplicate injections of the assay preparations were performed and the oxybutynin peak responses as area were recorded. The concentration of OC in the sample was calculated as described above. The concentration of OC in the sample was calculated as follows: [OC], mg/ml=[Std]$(A_{SX})(DF)/(A_{std})$, where [Std]=working standard concentration, mg/ml, $A_{SX}$= mean oxybutynin peak area in the assay preparation, $A_{std}$= mean oxybutynin peak area in the standard, DF=dilution factor. The results (Table 2) show that there is no significant degradation in OC over three weeks at 40° C. to 50° C.

TABLE 2

| Product ID | 0 time Oxybutynin Chloride % LC | 1 week Oxybutynin Chloride % LC | 3 week Oxybutynin Chloride % LC |
|---|---|---|---|
| RD186072-1 (40° C.) | 98.5 | 97.1 | 98.5 |
| RD186072-2 (40° C.) | 99.0 | 96.0 | 99.1 |
| RD186072-3 (40° C.) | 98.5 | 97.0 | 97.8 |
| RD186072-5 (40° C.) |  | Sample not taken | 98.4 |
| RD186072-1 (50° C.) | 98.5 | 96.1 | 99.3 |
| RD186072-2 (50° C.) | 99.0 | 94.5 | 100.1 |
| RD186072-3 (50° C.) | 98.5 | 95.8 | 98.0 |
| RD186072-5 (50° C.) | 97.9 | 97.0 | 98.1 |
| Reference | RD271009 | RD272072 | RD271044 |

% LC indicates the percentage of OC present as determined by HPLC.

EXAMPLE 2

Autoclave Stability Study

An autoclave feasibility study (Reference No. RD186072) was performed to determine if the OC solution could be autoclaved. This study was designed to determine the autoclavability of the product since the clinical samples are prepared in a similar manner as the final product. This terminal sterilization is an important process in the manufacturing process which has the potential to change the intrinsic nature of a product. Therefore, it is important to determine whether the product can be terminally sterilized.

Three formulations of OC solutions (RD186072-1, RD186072-2 and RD186072-3) were compounded and placed in 10 ml clear glass vials sealed with a TEFLON faced stopper. The filled units were autoclaved at 121° C. for 30 minutes. The autoclaved units were incubated at 40° C. for one week and assayed for OC. The results for zero time and one week autoclaved samples are shown in Table 3. The results indicate that the product can be autoclaved and that the product can then be stored without significant degradation of OC for 3 weeks at 40° C.

TABLE 3

| Product ID | 1 week Room Temp. Oxybutynin Chloride % LC | 1 week 40° C. Oxybutynin Chloride % LC | 3 week 40° C. Oxybutynin Chloride % LC |
|---|---|---|---|
| RD186072-1 Autoclaved | 95.5 | 95.2 | 98.5 |
| RD186072-2 Autoclaved | 98.2 | 98.5 | 99.1 |
| RD186072-3 Autoclaved | 99.9 | 96.1 | 97.8 |
| RD186072-5 Autoclaved | 96.2 | 95.7 | 98.4 |
| Reference | RD272072 | RD272072 | RD271044 |

EXAMPLE 3

Device Contact Study

A contact study was performed using various parts of an intravesical infuser which would come into contact with the OC solution during its use to determine whether any of the device contact parts would adversely affect the product. The contact study (RD1 86077) was performed to determine the effect of any contact between the product and the device materials and surfaces that may occur during usage of the product in the device.

OC Solution RD-1 86072-2 (Table 1) was compounded and placed in 10 ml clear glass vials sealed with a TEFLON spaced stopper. Prior to sealing the vials, the delivery device was taken apart and each contact part was placed in contact with 10 ml of the OC solution. The vials containing the contact parts and OC solution were stored at room temperature for one week. The solution was assayed at one week to determine if there was any decrease in the amount of OC in solution. The results (Table 4) indicate no significant change in the amount of OC when in contact with the device for one day at room temperature.

TABLE 4

| Product ID | Contact Part Material (amount in 10 mL) | 1 week Oxybutynin Chloride % LC | % Change |
|---|---|---|---|
| RD186077 | Control | 97.8 |  |
| RD186077-1 | End Cap Silicone (5 end caps) | 96.5 | −1.3 |
| RD186077-2 | Film Nylon (2 films) | 97.3 | −0.5 |
| RD186077-3 | Sleeve Retainer Ultem (4 retainers) | 92.3 | −5.5 |
| RD186077-4 | Suture Suture (5 sutures) | 94.2 | −3.6 |
| RD186077-5 | Black Flow Retainer Black Silicon (5) | 93.5 | −4.3 |
| RD186077-6 | Green Valve Green Silicon (5) | 94.6 | −3.2 |
| RD186077-7 | Silicone Tubing Clear silicone (2 tubes cut up) | 95.1 | −2.7 |
| Reference |  | RD272072 |  |

EXAMPLE 4

Dissolution Study

During formulation of the samples for lab stability, it was noticed that the OC is not freely soluble in water and that the pH had to be constantly adjusted to below 4.00 for the OC to dissolve. A dissolution study (RD186079) was performed to determine the solubility of OC at various pHs.

A 20 mg/ml solution of OC was compounded and the pH of the compounded solution was adjusted to pH 5, 6, and 7 with 1 N HCl and 1 N NaOH. Samples were taken at three different pH levels. Each sample was filtered through a 0.45 μm filter and the filtrate was assayed for the amount of dissolved OC. The results from the solubility study (Table 5) indicate that OC has a limited solubility at a pH >5.0.

TABLE 5

| Product ID | Oxybutynin Chloride |
|---|---|
| RD186087 (pH 4.0) | 88 mg/mL |
| RD186079-3A (pH 5.0) | 19.04 mg/mL |
| RD186079-3B (pH 6.0) | 2 mg/mL |
| RD186079-3C (pH 7.0) | <1.0 mg/mL |
| Reference | RD272072 |

EXAMPLE 5

Effect of Buffer Concentration on OC Precipitation

During the compounding of the lab stability samples, it was noticed that OC precipitated out of a solution buffered with 0.1 M citrate after one day at room temperature. The following study was performed to determine whether precipitation was dependent on buffer concentration. Two formulations of OC solution were compounded with different concentrations of citric acid and sodium citrate (0.01 M citrate, RD186083-2; 0.5 M citrate, RD186083-1) and assayed for OC content. The two formulations are shown in Table 8.

TABLE 6

| Reference Ingredient | RD186083-1 mg/mL | RD186083-2 mg/mL |
|---|---|---|
| Oxybutynin Chloride | 20.0 | 20.0 |
| Citric Acid | 6.00 | 1.20 |
| Sodium Citrate | 6.00 | 1.20 |
| 1N HCl/1N NaOH | qs pH to 4.00 | qs pH to 4.00 |
| Water For Injection | qs to 1 mL | qs to 1 mL |

The solution containing the 0.05 M citrate buffer precipitated out after one week after compounding at room temperature. This may be because the compounded solution was not filtered prior to filling. If any undissolved particles are present, this would initiate the crystallization process.

EXAMPLE 7

Solubility Study of OC Solution in Dog Urine

Solutions containing different concentrations of OC were added to dog urine (pH=6.5) to determine if and when OC starts precipitating out of solution. The different solutions that were compounded for the dog dose escalation study (Example 5), when added to dog urine, contained precipitated OC after the addition of a small (<1 ml) amount of solution to 25 ml dog urine, with the exception of the 2 mg/ml OC solution which did not show any precipitation even after the addition of 10 ml to 25 ml of dog urine. A 10 mg/ml OC solution was also added to 25 ml of dog urine and precipitation was observed after the addition of 1 ml of the solution.

It should be noted that the present invention is not limited to only those embodiments described in the Detailed Description. Any embodiment which retains the spirit of the present invention should be considered to be within its scope.

What is claimed is:

1. A pharmaceutical composition comprising an aqueous oxybutynin chloride solution, wherein said composition has an oxybutynin concentration of about 1.0 to 30 mg/ml and a pH of 3 to 5 is stable at about 37 degrees C for at least 12 hours, when placed within the bladder.

2. The composition of claim 1, wherein the concentration of oxybutynin chloride is between about 10 mg/ml and 25 mg/ml.

3. The composition of claim 2, wherein the concentration of oxybutynin chloride is about 20 mg/ml.

4. The composition of claim 1, wherein the pH is between about 3.5 and 4.5.

5. The composition of claim 4, wherein the pH is about 4.0.

6. The composition of claim 1, further comprising a buffering agent having a concentration of between about 0.005 M and 0.1 M.

7. The composition of claim 6, wherein said buffering agent has a concentration of between about 0.01 and 0.05 M.

8. The composition of claim 6, wherein said buffering agent is acetate or citrate.

9. The composition of claim 1, further comprising a viscosity-enhancing agent.

10. The composition of claim 9, wherein said viscosity-enhancing agent is carboxymethylcellulose or hydroxypropylmethylcellulose.

11. The composition of claim 1, further in combination with an infuser capable of releasing said composition at a predetermined flow rate.

12. The composition of claim 11, wherein said infuser is an intravesical infuser.

13. The composition of claim 11, wherein said flow rate is less than about 400 μl/hour.

14. A method for treating a bladder disorder, comprising the steps of:

positioning an intravesical infuser in said bladder; and introducing the pharmaceutical composition of claim 1 into said intravesical infuser.

15. The method of claim 14, wherein said bladder disorder is selected from the group consisting of secondary urge incontinence, hyperreflexive voiding dysfunction, neurogenic bladder and decreased bladder capacity.

16. The method of claim 14, further comprising the step of infusing said composition out of said infuser into the bladder at a rate not exceeding 400 1μ/hour.

* * * * *